(12) United States Patent
Liu

(10) Patent No.: US 10,463,301 B2
(45) Date of Patent: Nov. 5, 2019

(54) WEARABLE DEVICE BAND

(71) Applicant: ZTE Corporation, Shenzhen (CN)

(72) Inventor: Ming Liu, Shenzhen (CN)

(73) Assignee: ZTE Corporation, Shenzhen (CN)

( * ) Notice: Subject to any disclaimer, the term of this patent is extended or adjusted under 35 U.S.C. 154(b) by 0 days.

(21) Appl. No.: 15/775,793

(22) PCT Filed: Nov. 13, 2015

(86) PCT No.: PCT/CN2015/094615
§ 371 (c)(1),
(2) Date: May 11, 2018

(87) PCT Pub. No.: WO2017/079981
PCT Pub. Date: May 18, 2017

(65) Prior Publication Data
US 2018/0325451 A1     Nov. 15, 2018

(51) Int. Cl.
*A61B 5/00* (2006.01)
*G06F 1/16* (2006.01)
(Continued)

(52) U.S. Cl.
CPC .............. *A61B 5/681* (2013.01); *A61B 5/015* (2013.01); *A61B 5/02055* (2013.01); *A61B 5/7405* (2013.01); *A61B 5/7455* (2013.01); *A61B 5/7475* (2013.01); *G04C 3/001* (2013.01); *G04G 19/12* (2013.01); *G04G 21/00* (2013.01); *G04G 21/025* (2013.01); *G04G 21/08* (2013.01); *G06F 1/163* (2013.01); *G06F 1/1694* (2013.01); *G06F 3/016* (2013.01); *G06F 3/03* (2013.01); *H04M 19/04* (2013.01); *A61B 5/02438* (2013.01); *A61B 2562/0261* (2013.01);
(Continued)

(58) Field of Classification Search
CPC ...... G04C 3/001; G04C 21/00; G04C 21/025; G04C 21/08; G06F 1/163; G06F 1/1694; G06F 3/016; G06F 3/03; A61B 5/681; A61B 5/015; A61B 5/02055; A61B 5/7405; A61B 5/7455; A61B 5/7475
See application file for complete search history.

(56) References Cited

U.S. PATENT DOCUMENTS 5,615,179 A  *  3/1997  Yamamoto .......... G04G 17/083
                                              224/168
7,107,790 B2     9/2006  Frank
(Continued)

FOREIGN PATENT DOCUMENTS

WO    WO-2015168052 A1 * 11/2015 ............. A47F 7/022

OTHER PUBLICATIONS

International Search Report in international application No. PCT/CN2015/094615, dated Aug. 11, 2016.
(Continued)

*Primary Examiner* — Steven Lim
*Assistant Examiner* — Mancil Littlejohn, Jr.
(74) *Attorney, Agent, or Firm* — Oppedahl Patent Law Firm LLC

(57) ABSTRACT

A wearable device is disclosed. The wearable device may include a body. The wearable device may also include a band coupled with the body. The band may include a signal generator configured to generate a signal indicating a change of a shape of the band.

16 Claims, 11 Drawing Sheets

(51) Int. Cl.
*G06F 3/01* (2006.01)
*H04M 19/04* (2006.01)
*A61B 5/01* (2006.01)
*A61B 5/0205* (2006.01)
*G04G 21/08* (2010.01)
*G04G 19/12* (2006.01)
*G04G 21/00* (2010.01)
*G04C 3/00* (2006.01)
*G04G 21/02* (2010.01)
*G06F 3/03* (2006.01)
*A61B 5/024* (2006.01)
*G06F 3/041* (2006.01)

(52) U.S. Cl.
CPC . *A61B 2562/0271* (2013.01); *A61B 2562/043* (2013.01); *G06F 3/041* (2013.01)

(56) References Cited

U.S. PATENT DOCUMENTS

| | | | |
|---|---|---|---|
| 7,191,586 B2 * | 3/2007 | Yamamoto | A44C 5/105 59/80 |
| 7,201,020 B2 | 4/2007 | Frank | |
| 9,553,625 B2 * | 1/2017 | Hatanaka | H04M 19/047 |
| 9,693,609 B2 * | 7/2017 | Rohrbach | G04B 37/1486 |
| 2005/0076674 A1 * | 4/2005 | Frank | A44C 5/14 63/9 |
| 2005/0193767 A1 | 9/2005 | Frank | |
| 2014/0378113 A1 * | 12/2014 | Song | G06F 3/014 455/418 |
| 2015/0091711 A1 | 4/2015 | Kosonen et al. | |
| 2015/0145673 A1 | 5/2015 | Choi et al. | |
| 2015/0227245 A1 * | 8/2015 | Inagaki et al. | G06F 3/0412 345/173 |
| 2016/0255944 A1 * | 9/2016 | Baranski | A44C 5/0069 |
| 2017/0086742 A1 * | 3/2017 | Harrison-Noonan | A61B 5/6843 |

OTHER PUBLICATIONS

Written Opinion of the International Search Authority in international application No. PCT/CN2015/094615, dated Aug. 11, 2016.

* cited by examiner

WEARABLE DEVICE BAND

TECHNICAL FIELD

This disclosure relates generally to wearable devices. More specifically, it relates to a band of a wearable device capable of automating certain functions based on the shape or a change of the shape of the band or based on a relative position between the band and a body of the wearable device.

BACKGROUND

Wearable devices have become widely used by consumers due to their small size and some smart functionalities. Among the wearable devices, smart watches are often seen as the most developed and the most advanced type of wearable devices on the market. While many advances have been made to improve the functionality and utility of the smart watches, one challenge faced by the smart watch R&D community is how to provide effective interaction between a user and his/her smart watch. In the case of smart phones, currently the most common interaction method is through the display of a smart phone, where a user can provide input by touching on a touch screen, which is available in most smart phones. This traditional method is, however, not very convenient in the context of a smart watch because the small display size of a typical smart watch is not suitable for effective touching and typing. Therefore, it is desirable to provide a wearable device with a more convenient interaction method.

SUMMARY

In one aspect, the present disclosure is directed to a wearable device. The wearable device may include a body. The wearable device may also include a band coupled with the body. The band may include a signal generator configured to generate a signal indicating a change of a shape of the band.

In another aspect, the present disclosure is directed to a wearable device. The wearable device may include a body. The wearable device may also include a band coupled with the body. The band may include a signal generator configured to generate a signal indicating a change of a relative position between the band and the body.

In a further aspect, the present disclosure is directed to a band. The band may include first and second bracelet links. The band may also include a connection pin linking the first and second bracelet links. The band may also include a sensor configured to detect a relative position or a change of the relative position between the first and second bracelet links.

In a further aspect, the present disclosure is directed to a band coupled to a wearable device. The band may include a sensor configured to detect a shape or a change of the shape of the band.

In a further aspect, the present disclosure is directed to a band coupled to a wearable device. The band may include a sensor configured to detect a change of a relative position between the band and the wearable device.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

it is to be understood that the foregoing general description and the following detailed description are exemplary and explanatory only, and are not restrictive of the invention, as claimed.

BRIEF DESCRIPTION OF THE DRAWINGS

The accompanying drawings, which constitute a part of this specification, illustrate several embodiments and, together with the description, serve to explain the disclosed principles.

DETAILED DESCRIPTION

Figure 1:
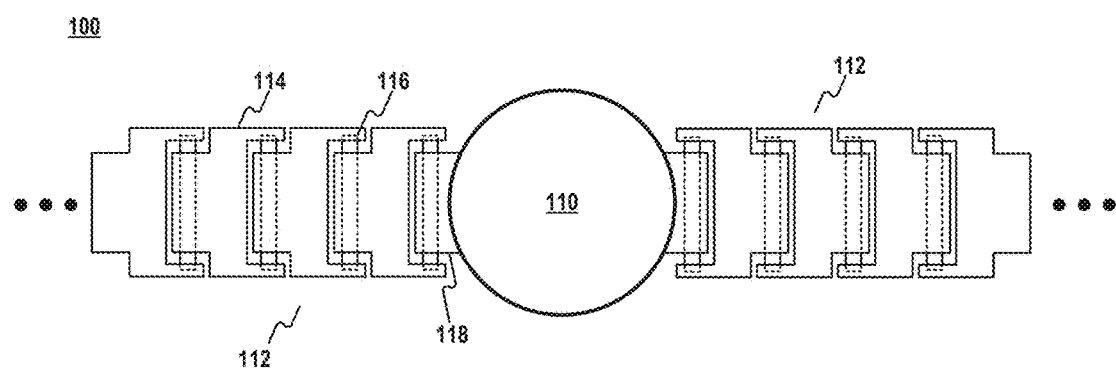
FIG. 1 is a schematic diagram of an exemplary watch, according to some embodiments of the present disclosure.

Reference will now be made in detail to exemplary embodiments of the invention, examples of which are illustrated in the accompanying drawings. When appropriate, the same reference numbers are used throughout the drawings to refer to the same or like parts.

Embodiments consistent with the present disclosure involve a wearable device. A wearable device, as used herein, refers to a device that can be worn by a user as clothing or an accessory. The wearable device can be functional and/or fashionable. The wearable device can be worn on, for example, a wrist, an arm, an ankle, a leg, an ear, the neck, the forehead, or other places of the user. In some embodiments, wearable devices may incorporate computer and/or electronic technologies. Exemplary wearable devices include watches (e.g., smart watches), activity trackers, smart glasses, sleep trackers, smart jewelries, earbuds, head-mount optical display, etc.

A wearable device may include a device body and a band coupled with each other. As used herein, the term "couple" includes mechanically, electrically, and/or communicatively connecting one object with another object. For example, the device body and the band may be mechanically and/or electrically connected with each other. In another example, the device body and the band may be communicatively connected with each other through a wired or wireless communication link. The device body may include a physical enclosure enclosing mechanical and/or electrical components. The band may include mechanism for a user to "wear" the device body. As used herein, the term "wear" may include affixing, attaching, enclosing, or otherwise associating the device body with at least a body part of the user using, for example, the band.

An exemplary wearable device may be in the form of a watch. While watches are traditionally used as time keepers, the term "watch" used herein may or may not have a time keeping or time calculating function. For example, watches may include activity trackers, GPS trackers, sleep trackers, etc.

A watch having some computational power may be referred to as a smart watch. The computational power may be provided or implemented by one or more microprocessors, electronic devices, circuits, or other hardware components. In some embodiments, a smart watch may be capable of running one or more software applications. The hardware, software, or the combination thereof may provide communication, notification, entertainment, or other functionalities. In some embodiment, a smart watch may include devices such as a microprocessor, a memory (e.g., a RAM, a flash memory, etc.), a display device (e.g., an LCD screen, an LED display, an OLED display, a touch screen, etc.), a battery device, a communication interface (e.g., wireless connection such as WiFi, Bluetooth, GPS, 3G/4G/LTE, etc.), and/or input/output devices (e.g., buttons, touch screen, pressure sensor, audio device, vibration device, etc.). Watches having limited or special functionality such as activity trackers, GPS trackers, or sleep trackers described above may also be referred to as smart watches.

As an exemplary wearable device, watch may generally include two main parts: a watch body and a band. The watch body refers to the main body of the watch that encloses the majority of the hardware for providing the various features of the watch. Usually the watch body assumes a shape of a block and includes a watch face, which may be in the form of a display. In some embodiments, the display is touch sensitive (e.g., a touch screen) and/or pressure sensitive so that a user may input information using the display. The band refers to the part of the watch that affixes the watch onto a user's wrist (or other similar body parts such as arm, ankle, leg, etc.). In some embodiments, the band may be in the form of an oyster-style bracelet including a plurality of interconnected bracelet links. In some embodiments, the band may be in the form of a two-piece band, each piece having one end attached to the watch body and the other end fixable to each other. In some embodiments, the band may be in the form of a one-piece band with both ends attached to the watch body, where the one-piece band may be flexible and stretchable to allow a user to wear the watch. The material of the band may vary depending on particular type of the band. Examples may include metal (e.g., in case of oyster-style bracelet), leather, fabric, rubber, plastic, etc.

FIG. 1 is a schematic diagram of an exemplary watch 100, according to some embodiments of the present disclosure. Watch 100 may include a watch body 110 and a band 112. As shown in FIG. 1 band 112 may be an oyster-style bracelet including a plurality of interconnected bracelet links 114. Two adjacent bracelet links may be coupled (e,g., mechanically connected) with each other by a connection pin 116.

While FIG. 1 shows band 112 as two pieces, i.e., a two-pieces band, the left and right parts of band 112 may be joint by a clasp buckle to form a one-piece structure. Watch 100 may include a block-shaped connecting part 118 extending on both sides of watch body 110. Block-shaped connecting part 118 may be used to connect band 112 to watch body 110 by holding a center portion of connection pin 116, similar to the connection manner between adjacent bracelet links.

Figure 2:
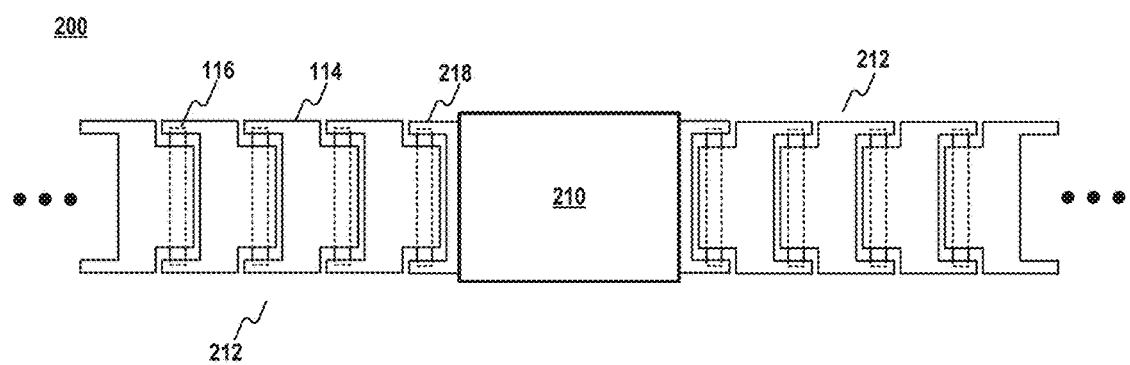
FIG. 2 is a schematic diagram of another exemplary watch, according to some embodiments of the present disclosure.

FIG. 2 is a schematic diagram of another exemplary watch 200, according to some embodiments of the present disclosure. Watch 200 may include a watch body 210 and a band 212. While watch body 110 shown in FIG. 1 has a round shape, watch body 210 has a rectangular shape. The particular shape of a watch body, however, can vary from case to case. The examples shown in FIGS. 1 and 2 provide two typical shapes but other shapes may also be used. The technical solution disclosed herein is not limited to a particular shape of the watch body. Band 212 may be a similar oyster-style bracelet to band 112, except that the direction of individual bracelet links of band 212 is different from that of band 112. The change of direction is due to a different connection part 218 used in watch 200. Here, connection part 218 includes two distal parts for receiving both ends of connection pin 116 instead of holding the center portion of connection pin 116. Similar to watch band 112, the left and right parts of band 212 may be joined by a clasp buckle to form a one-piece structure.

Figure 3:
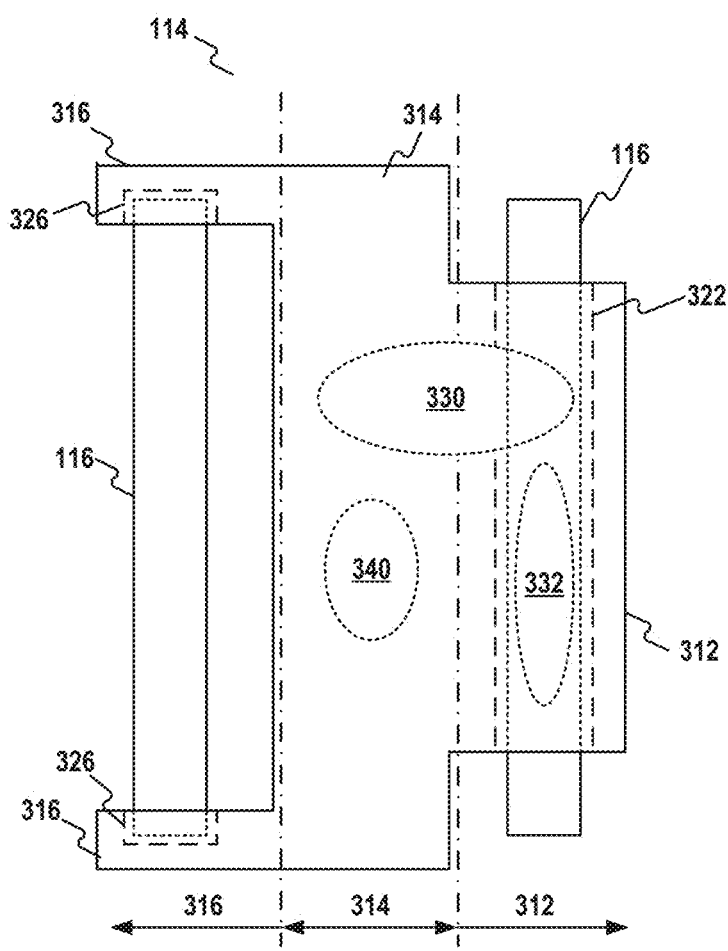
FIG. 3 is a schematic diagram of an exemplary bracelet link, according to some embodiments of the present disclosure.

FIG. 3 is a schematic diagram of an exemplary bracelet link 114, according to some embodiments of the present disclosure. As shown in FIG. 3, bracelet link 114 may generally include three portions: a head portion 312, a center portion 314, and a distal or tail portion 316. The dash-dot lines in FIG. 3 provide a rough division of these three portions, which is also indicated at the bottom part of FIG. 3. In some embodiments, head portion 312, center portion 314, or the collection of these two portions may also be referred to as a block portion. In some embodiments, center portion 314 may be merged to head portion 312 to form a single portion.

As shown in FIG. 3, head portion 312 may include a through hole 322. Through hole 322 may be used to allow insertion of a connection pin 116 and to hold the inserted connection pin 116 in place. Distal portion 316 may include two parts, each including a receiving hole 326. Receiving holes 326 may be opposite to each other and configured to receive both ends of another connection pin 116 (e.g., a different connection pin from the one passing the through hole 322) to secure that connection pin 116 in place.

The block portion (e.g., head portion 312, center portion 314, or the combination thereof) may include a sensing device 330. Sensing device 330 may, either alone or in combination with another sensing device 332 included in connection pin 116, sense a motion of bracelet link 114 with respect to an adjacent bracelet link. In some embodiments, sensing devices 330 and 332 may form a sensor configured to generate a sensing signal based on the motion. The strength or value of the sensing signal may depend on the property of the motion.

The sensing signal may be received by a signal transmitter 340. Signal transmitter 340 may be included in bracelet link 114 (e.g., in any portion or across multiple portions), as shown in FIG. 3 In some embodiments, signal transmittal may be included in the connection pin 116, in a different bracelet link, or in the watch body 110/210. In some embodiments, signal transmitter 340 may determine whether the strength or value of the sensing signal is above a predetermined threshold. If so, signal transmitter 340 may transmit a signal to, for example, a processor for further processing. If not, signal transmitter 340 may record the current sensing signal without transmitting any signal to the processor. In some embodiments, signal transmitter may transmit a signal to the processor whenever a sensing signal is received, regardless of the strength or value of the sensing signal. The processor may be included in the watch body 110/210, in the band 112/212, or in a terminal device or a peripheral device external to watch 100/200.

Figure 4:
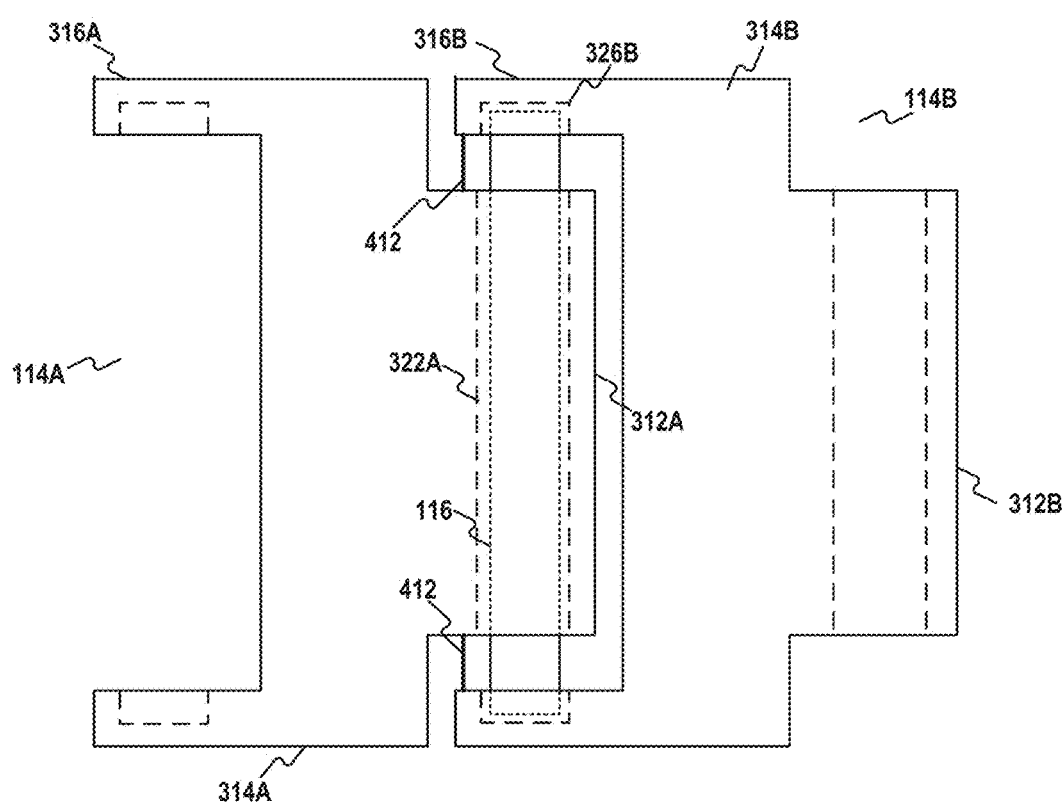
FIG. 4 is a schematic diagram of an exemplary bracelet link assembly, according to some embodiments of the present disclosure.

FIG. 4 is a schematic diagram of an exemplary bracelet link assembly, according to some embodiments of the present disclosure. The bracelet link assembly shown in FIG. 4 includes two bracelet links: 114A and 114B. Similar to bracelet link 114 shown in FIG. 3, bracelet link 114A may include a head portion 312A, a center portion 314A, and a distal portion 316A, and bracelet link 114B may include a head portion 312B, a center portion 314B, and a distal portion 316B. Bracelet links 114A and 114B may be coupled (e.g., mechanically connected) with each other by a connection pin 116. Head portion 312A may include a through hole 322A. Connection pin 116 may pass through the through hole 322A and rotationally fitted inside hole 322A. The two ends of connection pin 116 may be received by receiving holes 326B in the distal portion 316B of bracelet link 114B. Connection pin 116 may be secured and held in place by distal portion 316B. For example, the two ends of connection pin 116 may be rigidly fitted in receiving holes 326B such that connection pin 116 may rotate together and in concert with bracelet link 114B with respect to bracelet link 114A.

The bracelet link assembly shown in FIG. 4 may include a wire connection 412 between bracelet links 114A and 114B. For example, wire connection 412 may be located between distal portion 316B and head portion 312A. In some embodiments, wire connection 412 may be provided at both sides of head portion 312A. In other embodiments, wire connection 412 may be provided at either one side of head portion 312A. In some embodiments, wire connection 412 may be provided at any part of the band may extend along and across some portions of the band. For example, wire connection 412 may be embedded in the watch band when the watch band is at least partially continuous. Wire connection 412 may be used to supply power to sensing devices 330/332 and/or signal transmitter 340. Wire connection 412 may also be used to electrically connect signal transmitter 340 to a processor. For example, wire connection 412 may connect the signal transmitter of every bracelet link in series, in parallel, or a combination thereof. In some embodiment, wire connection 412 may be used as a connection sensor to detect disconnection between two adjacent bracelet links or between a bracelet link and the watch body. For example, when the bracelet links are connected in series by wire connection 412, a loss of signal may indicate a disconnection.

Figure 5:
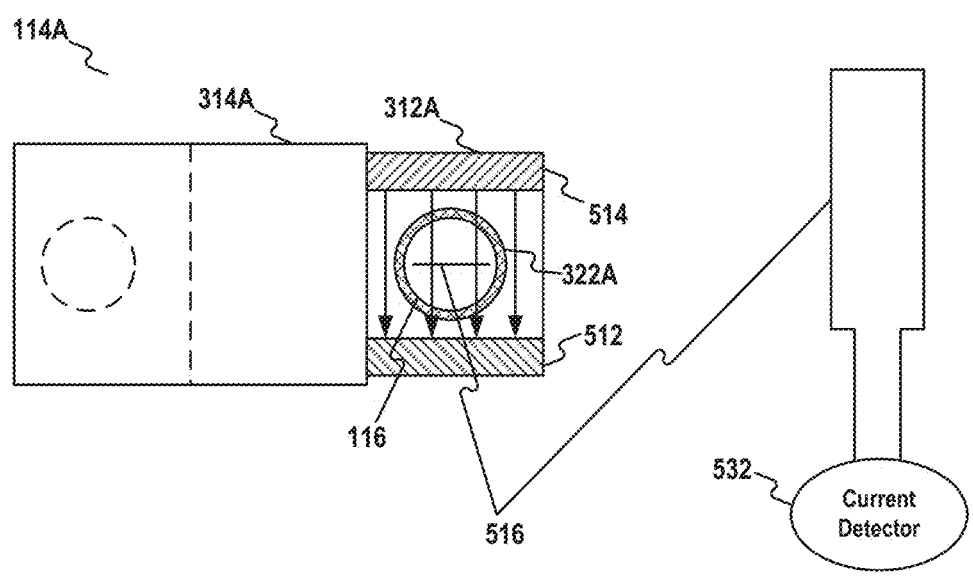
FIG. 5 is a schematic diagram of an exemplary sensor, according to some embodiments of the present disclosure.
Figure 6:
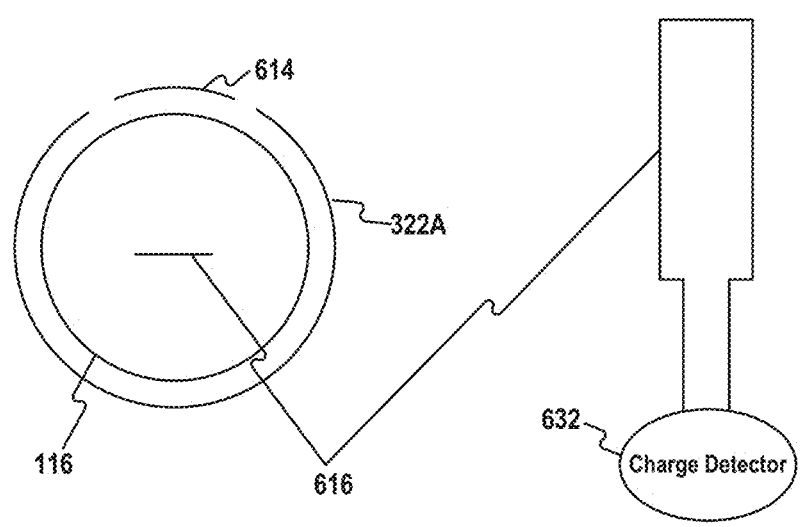
FIG. 6 is a schematic diagram of another exemplary sensor, according to some embodiments of the present disclosure.
Figure 7:
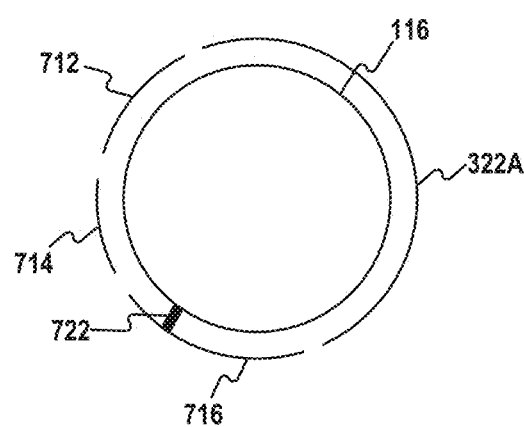
FIG. 7 is a schematic diagram of another exemplary sensor, according to some embodiments of the present disclosure.

Referring back to FIG. 3, the sensor formed by sensing device 330 in the block portion and sensing device 332 in connection pin 116 may be a position sensor. For example, the position sensor may detect the motion of bracelet link 114A with respect to bracelet link 114B, thereby detecting a change of the relative position between these two bracelet links. In some embodiments, the relative position between two bracelet links may include the relative angle between the two bracelet links when the detected motion is a rotating motion. In this case, the position sensor may be an angle sensor. In some embodiments, the relative position may include a relative distance when the detected motion is a linear displacement. In this case, the position sensor may be a distance sensor (e.g., based on magnetic sensing). In some embodiments, the sensor may be integrated in the block portion and/or connection pin 116. FIGS. 5-7 show three embodiments of the position sensor according to different physical principles.

FIG. 5 shows an exemplary position sensor (e.g., an angle sensor) based on induction current generation (Faraday's law). FIG. 5 shows a side view of bracelet link 114A (FIG. 4 shows the top view). As shown in FIG. 5, head portion 312A may include a magnetic device comprising, for example, a first magnet 512 and a second magnet 514. Magnets 512 and 514 may be integrated into the bottom and top parts of head portion 312A, respectively. Magnets 512 and 514 may be opposite in polarity. For example, FIG. 5 shows an N magnet 514 and an S magnet 512, such that a magnet field is established between magnets 514 and 512. In some embodiments, head portion 312A, including through hole 322A, and connection pin 116 may be made of material that is non-disruptive to the magnetic field, such as electrical insulating material. As a result, the magnetic field is also established inside connection pin 116, as shown in FIG. 5.

A wire 516 made of electrically conductive material may be integrated in the connection pin. Wire 516 may form a loop enclosing a 2D plane through which magnetic field lines can pass. In some embodiments, the 2D plane enclosed by the wire loop 516 may be substantially perpendicular to the magnetic field lines when bracelet links 114A and 114B are substantially aligned with each other (e.g., they form a zero-degree angle). When the relative angle between bracelet links 114A and 114B changes (e.g., when bracelet link 114B rotates with respect to bracelet link 114A), connection pin 116 may also rotate such that wire 516 may cut the magnetic field lines and, induction current will be generated. A current detector 532 may be used to detect the induction current as an indication of the degree of rotation experienced by connection pin 116. Current detector 32 may be part of sensing device 330 or part of signal transmitter 340.

FIG. 6 shows another exemplary position sensor (e.g., an angle sensor) based on changes in capacitance. As shown in FIG. 6, a capacitor may be formed between the surface of through hole 322A and connection pin 116. For example, a first panel 614 of the capacitor may be integrated into a portion of the surface of through hole 322A. A second panel 616 of the capacitor may be integrated in the connection pin 116. A constant voltage may be maintained between first panel 614 and second panel 616. When both panels are substantially parallel to each other, the capacitor formed by panels 614 and 616 has a certain capacitance. When the relative angle between two adjacent bracelet links changes, the relative angle between panels 614 and 616 also changes, thereby changing the capacitance of the capacitor. Since the voltage between the two panels is kept constant, the change of capacitance will change the electrical charges held by the capacitor. Therefore, detecting the change of electrical charges using a charge detector 632 can indicate the change of relative angle between the two adjacent bracelet links.

FIG. 7 shows another exemplary position sensor (e.g., an angle sensor) based on changes in resistance. As shown in FIG. 7, the surface of through hole 322A may be formed by a plurality of resistors 712, 714, 716, etc. The plurality of resistors may have different resistance. The resistors may be resistor strips that extend along the axial direction of connection pin 116. Adjacent resistors may be separated by an insulator. The outer surface of connection pin 116 may also be made of insulating material. A contacting member 722 made of conductive material may be included on the outer surface of connection pin 116. Contacting member 722 may contact the surface of through hole 322A, including the plurality of resistors 712, 714, 716, etc. When contacting member 722 contacts a particular resistor, a particular resistance will result. Therefore, the angle information can be indicated from the resistance information. In this embodiment, the relative angle between two bracelet links may be directly determined based on the resistance information if a mapping relationship between angles and resistance values is established. The change of the relative angle may also be detected when the resistance information indicates a change in the resistance values.

Figure 8:
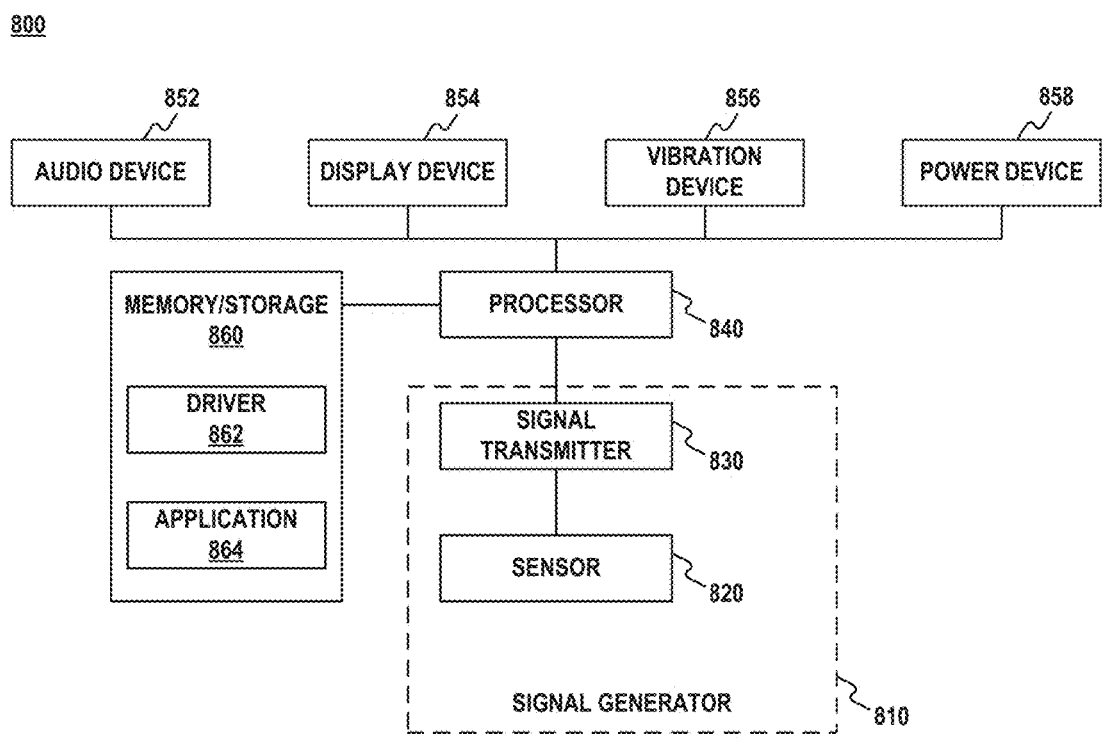
FIG. 8 is a functional block diagram of an exemplary watch, according to some embodiments of the present disclosure.

FIG. 8 is a functional block diagram of an exemplary watch 800, according to some embodiments of the present disclosure. For example, watch 800 may be a functional representation of any one of watch 100, 200, or 1000 (shown in FIG. 10). Watch 800 may include a signal generator 810. In some embodiments, signal generator 810 may be integrated into a band of watch 800. Signal generator 810 may include a sensor 820 (e.g., 330 and/or 332) and a signal transmitter 830 (e.g., 340). Sensor 820 may detect the shape of the watch band or a change of the shape of the watch band. For example, sensor 820 may include sensing devices 330 and 332 to sense a relative position or a change of relative position between two adjacent bracelet links using position detecting technique shown in FIGS. 5, 6, or 7. When any two adjacent bracelet links change their relative position, sensor 820 may generate a sensing signal. The sensing signal may be received by signal transmitter 830. Signal transmitter 830 may determine whether the sensing signal is above a predetermine threshold, indicating the two bracelet links undergo a relative large change in relative position. If so, signal transmitter 830 may transmit a signal to processor 840. If not, signal transmitter may not transmit the signal to processor 840 and may record the current position information based on the sensing signal. In some embodiments, signal transmitter 830 may transmit the signal to processor 840 whenever a sensing signal is received. Processor 840 may be included in the watch body, the band, or a terminal/peripheral device external to watch 800. Processor 840 may be connected to signal transmitter 830 through, for example, wire connection 412. In some embodiments, processor 840 may be connected to signal transmitter 830 through a wireless communication link (e.g., WiFi, Bluetooth, etc.).

In some embodiments, the band may include a plurality of bracelet links, and each bracelet link may be assigned a number. Each bracelet link may include a signal generator 810, and each signal generator 810 may generate a signal when its corresponding bracelet link and an adjacent bracelet link undergo a change in relative position. Processor 840 may receive these signals from individual signal generators. Processor 840 may determine the current shape of the band based on the signals from individual signal generators and their assigned numbers. For example, when the number or percentage of signal generators that transmit signals to processor 840 is above a threshold (e.g., over 30% or 40%), indicating that a substantial number of bracelet links is undergoing relatively large change, processor 840 may send a request to all signal generators to request the current position information of its corresponding bracelet link. Based on the position information of all bracelet links and their assigned numbers, processor may determine the current shape of the band.

In some embodiments, processor 840 may determine the current shape of the band based on signals received from individual signal generators without first determining the threshold number of signal transmitting signal generators.

For example, sensing signals generated by a sensor (e.g., sensor 820) of each individual bracelet link may be received by processor 840 through signal transmitter 830 without preprocessing (e.g., signal transmitter 830 may be in the form of a wired connection between sensor 820 and processor 840). Processor 840 may then process the sensing signals and determine position information between adjacent bracelet links. Based on the position information, processor 840 may determine the current shape of the band.

Figure 11:
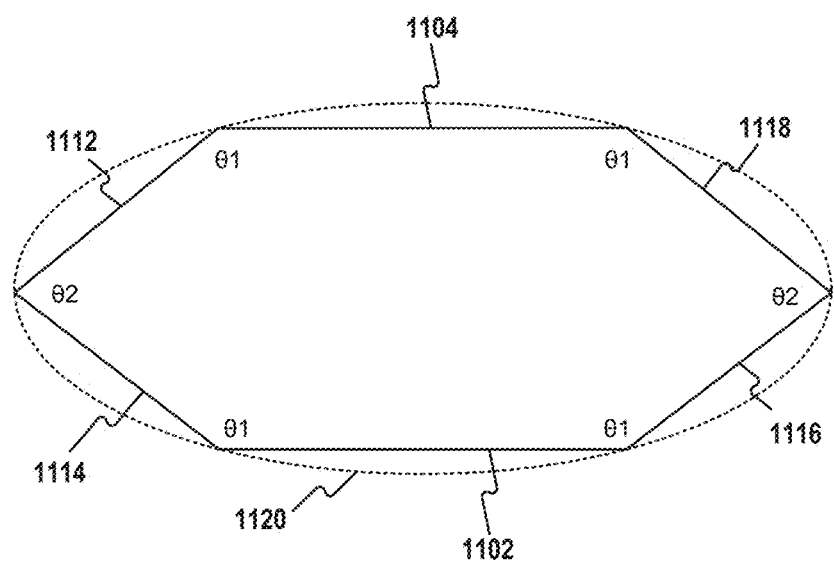
FIG. 11 is a schematic diagram of an exemplary method for determining the shape of a band, according to some embodiments of the present disclosure.

FIG. 11 is a schematic diagram of an exemplary method for determining the shape of a band. As shown in FIG. 11, a simplified watch may include a watch body 1104, a band including four portions 1112, 1114, 1116, and 1118 (e.g., each portion may be a bracelet link), and a buckle 1102. Assume that the length of the watch body 1104 and the buckle 1102 is a (e.g., the linear length when viewing the watch from its side and the length of each portion of the band is $$\frac{\sqrt{a^2 + 3b^2}}{2},$$

then the shape of the watch may be a hexagon tangential to an ellipse 1120 when a user is wearing the watch. The length of the semi-major axis of ellipse 1120 is a and the length of the semi-minor axis of ellipse 1120 is b. Assume that the angles between a band portion (1112, 1114, 1116, or 1118) and the watch body/buckle (1104/1102) are all the same and denoted as $\theta_1$, and the angles between adjacent band portions are the same and denoted as $\theta_2$, then $\theta_1$ and $\theta_2$ can be expressed as follows:

$$\theta_1 = \arctan\frac{\sqrt{3}}{2} + 90°; \text{ and } \theta_2 = 180° - 2\arctan\frac{\sqrt{3}}{2}.$$

The angle information (e.g., $\theta_1$ and $\theta_2$) may be detected by sensor 820. Processor 840 may compare the value of the detected angle with the target value (e.g., as shown in the above equations) and determine that the watch's approximate shape to be a hexagon tangential to an ellipse when the compared difference is within a preset threshold.

Various shapes may be used to calculate the angle parameters for comparing with the detected angle information. Mapping relationship may be established to associate certain detect signal(s) or sets of signals with a particular shape. In some embodiments, processor 840 may also calculate the shape of the watch based on the detected signal (e.g., angle, position, etc.) and the size/arrangement of the band.

Based on the determined shape, processor 840 may generate a response. For example, when it is determined that the shape of the watch band is roughly elliptical, it may indicate that the use is wearing the watch on his/her wrist, and processor 840 may control power device 858 to power on the watch. In another example, if it is determined that the shape of the watch band is irregular, it may indicate that the user has taken off the watch, and processor 840 may control power device 858 to power off the watch or enter into sleep or standby mode. In another example, if it is determined that the shape of the watch band has a flat bottom part and a curved or irregular upper part, it may indicate that the user is using the watch as an alarm clock, and processor 840 may control the watch to enter an alarm clock mode or launch an alarm clock application. For example, processor 840 may control display device 854 to display an alarm clock interface. Once the alarm goes off, and the shape of the watch band changes, it may indicate that the user is picking up the watch, and processor 840 may stop the alarm and control the watch to exit the alarm clock mode. In another example, when it is determined that a disconnection between two bracelet links occurs (e.g., wire connection 412 disconnects), controller 840 may control audio device 852 to generate an audio alarm, control vibration device 856 to generate vibrations, or control display device 854 to display alarm information (e.g., using high brightness settings).

Processor 840 may implement the above functions by accessing memory/storage device 860. For example, memory/storage device 860 may store driver 862 and application 864. Driver 862 may include program to facilitate data communication between processor 840 and signal generator 810. Application 864 may include program to implement various algorithms and control logics to process and respond to signals received from signal generator 810.

Figure 9:
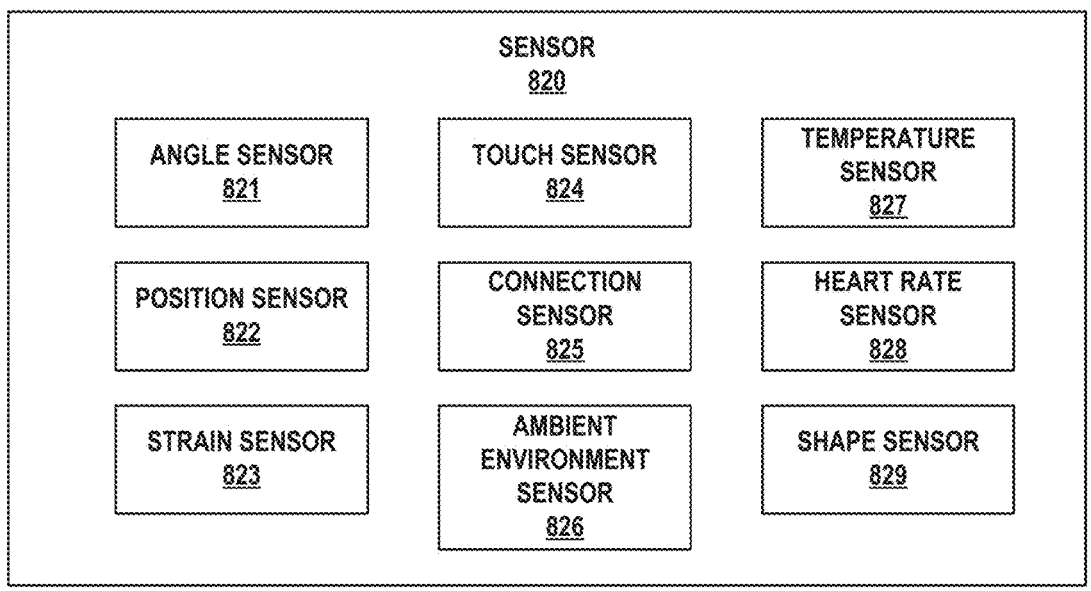
FIG. 9 is functional block diagram of an exemplary signal generator, according to some embodiments of the present disclosure.

FIG. 9 shows a functional block diagram of sensor 820. As shown in FIG. 9, sensor 820 may include one or more types of sensors. For example, sensor 820 may include an angle sensor 821 and/or a position sensor 822, such as sensors shown in FIGS. 5-7. Sensor 820 may include a strain sensor 823, which will be discussed in connection with FIG. 10. Sensor 820 may include a touch sensor 824. Touch sensor 824 may be used for detecting a touch action on a surface of the band. A user may interact with the watch by touching or swapping on the surface of the band. Sensor 820 may include a connection sensor 825, such as wire connection 412. Connection sensor 825 may be used to detect a disconnection between bracelet links or between watch body and watch band. Sensor 820 may also include an ambient environment sensor 826. Sensor 826 may be used to detect, for example, air condition or air quality in the ambient environment. Sensor 820 may include multiple temperature sensor 827. The temperature sensors 827 may be located at different parts of the band for detecting a temperature distribution across the band. For example, when at least one of the temperature sensors indicates that the temperature is rising rapidly towards body temperature (e.g., towards 33° C. at a rate of 1° C. per minute or higher), processor 840 may determine that the user is wearing the watch and may control power device 858 to power on the watch. In another example, processor 840 may determine that the user is wearing the watch when multiple temperature sensors located at different parts of the band all indicate rapid temperature rise. Processor 840 may perform various functions based on the determination that the watch is being worn by the user, such as changing the display of the watch, generating an audible alarm, generating a vibration, stopping an alarm, launching an application, and/or entering into or existing from a predetermined mode when. Temperature sensor 827 may work together with other sensors in operation.

Sensor 820 may include a heart rate sensor 828. Heart rate 828 may be configured to detect a heartbeat signal of a user when the band is placed in close proximity of a body part of the user, e.g., when the user is wearing the watch on his/her wrist. The heart rate sensor may be placed on any part of the band or on the buckle portion that connects two pieces of the band. When heart rate sensor 828 detects that the heart rate approaches or is within a regular human heart rate range, processor 840 may determine that the user is wearing the watch and may power on the watch. On the other hand, when the detected heart rate is outside the regular human heart rate range, processor 840 may determine that the user is not wearing the watch and may power off the watch. Processor 840 may perform various functions based on the determination that the watch is being worn by the user, such as changing the display of the watch, generating an audible alarm, generating a vibration, stopping an alarm, launching an application, and/or entering into or existing from a predetermined mode when. Heart rate sensor 828 may work together with other sensors in operation.

Figure 10:
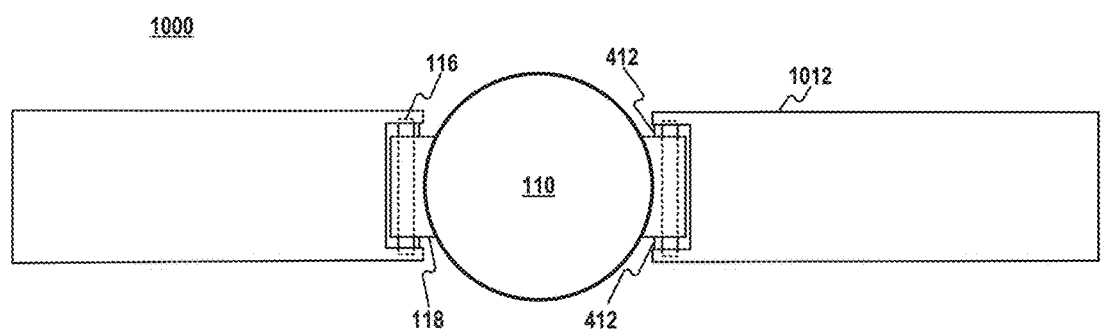
FIG. 10 is a schematic diagram of another exemplary watch, according to some embodiments of the present disclosure.

Sensor 828 may include a shape sensor 829. Shape sensor 829 may directly detect the shape of the band. For example, shape sensor 829 may be a shape-memory alloy extending along the band. The shape-memory alloy may have different resistance when it assumes different shapes. When the shape-memory alloy assumes a particular shape, for example, the original shape that it "remembers," the resistance of the shape-memory alloy may be a particular value. Therefore, processor 840 may determine the shape of the band based on resistance signal provided by the shape-memory alloy. Processor 840 may perform various functions based on the determination of the shape of the band, such as changing the display of the watch, generating an audible alarm, generating a vibration, starting/stopping an alarm, launching an application, powering on/off the watch, and/or entering into or existing from a predetermined mode when, FIG. 10 shows another example watch 1000. Watch 1000 is similar to watch 100, except that the watch band 1012 is not an oyster-style band. Instead, band 1012 may be a continuous piece and may be made of leather, rubber, fabric, or plastic. In one embodiment, band 1012 may include signal generator 810 only at the connections between the watch band and the watch body. In this case, the relative angle detected by sensor 820 is between band 1012 and watch body 110. Processor 840 may generate responses based on this relative angle information. For example, when both relative angles experience a large change (e.g., larger than 45 degrees) and then maintain within a predetermined range (e.g., from 90-12 degrees), it may indicate that the user is putting on the watch on his/her wrist, and processor 840 may control power device 858 to power on the watch. In another example, if either sensor detects that the angle between the watch and the band has been outside the predetermined range for a predetermined time (e.g., 10 seconds), then it may indicate that the user has taken off the watch and the processor 840 may control power device 858 to power off the watch or enter into sleep mode. In another example, the power off may also be triggered after detecting a relative large change in angle (e.g., larger than 60 degree) by the sensor on either side. In another example, the power off may be triggered when the summation of both angles is greater than a predetermined threshold.

As shown in FIG. 10, in one embodiment, the power supply may be located in the watch body 110, and wire connection 412 may be provided between band 1012 and watch body 110. Wire connection 412 may provide power to the sensors mentioned above. Furthermore, wire connection 412 may detect a disconnection between band 1012 and watch body 110, similar to the disconnection detection between two bracelet links. In one embodiment, the power supply may be located outside watch body 110. For example, the power supply may be included within watch band 1012, and wire connection 412 may be located in an appropriate place according to the location of the power supply.

In some embodiments, band 1012 may include a flexible surface, such as when the band is made of leather, rubber, fabric, plastic, etc. The flexible surface may be divided into a plurality of regions (not shown). Each region may be assigned a number. In addition, each region may include a strain sensor 823 Strain sensor 823 may generate a resistance signal based on a degree of deformation of that region. The sign of the resistance signal may indicate the direction of deformation. The combination of the deformation information, together with their numbers, may be used to determine the shape of the band.

The specification has described exemplary watches, bands, and methods of operating the watch(s) based on signals received from the band(s). The illustrated steps are set out to explain the exemplary embodiments shown, and it should be anticipated that ongoing technological development will change the manner in which particular functions are performed. Thus, these examples are presented herein for purposes of illustration, and not limitation. For example, steps or processes disclosed herein are not limited to being performed in the order described, but may be performed in any order, and some steps may be omitted, consistent with disclosed embodiments.

Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a", "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include RAM, ROM, volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A wearable device, comprising:
    a body;
    a band coupled with the body; and
    a signal generator configured to generate a signal indicating a change of a shape of the band;
    wherein the signal generator comprises a sensor configured to detect the change of the shape of the band;
    wherein the band comprises first and second bracelet links coupled to each other by a connection pin;
    wherein at least part of the sensor is integrated in at least one of the first bracelet link or the connection pin;
    wherein the sensor is configured to detect a change in a relative position between the first and second bracelet links; wherein the relative position between the first and second bracelet links includes a relative angle between the first and second bracelet links.

2. The wearable device of claim 1, comprising a processor device configured to:
    receive the signal; and
    generate a response based on the signal,
    wherein the processor device is included in the body or the band, or is located on a terminal device or a peripheral device external to the wearable device.

3. The wearable device of claim 2, wherein the response comprises at least one of:
    a change of display on a display device of the body;
    generating an audible alarm;
    generating a vibration;
    entering into or exiting from a predetermined mode;
    launching an application; or
    powering on or off of the wearable device.

4. The wearable device of claim 1, wherein the sensor comprises:
    a magnetic device integrated in the first bracelet link to establish a magnetic field in the connection pin; and
    a wire made of electrically conductive material integrated in the connection pin, wherein the wire generates an electrical current by moving in the magnetic field when the relative angle between the first and second bracelet links changes.

5. The wearable device of claim 1, wherein the sensor comprises:
    a capacitor including first and second panels, the first panel being integrated in the first bracelet link and the second panel being integrated in the connection pin, wherein the first and second panels of the capacitor are configured to cause a change of electrical charges held by the capacitor when the relative angle between the first and second bracelet links changes.

6. The wearable device of claim 1, wherein the sensor comprises:
    a plurality of resistors integrated in the first bracelet link, the plurality of resistors having different resistance values; and
    a contacting member on an outer surface of the connection pin, wherein the contacting member is configured to contact one of the plurality of resistors when the first and second bracelet links form a particular angle.

7. The wearable device of claim 1, wherein:
    the band includes a flexible surface divided into a plurality of regions; and
    the signal generator includes a plurality of strain sensors, each being included in one of the plurality of regions and configured to generate a resistance signal based on a degree of deformation of that region.

8. The wearable device of claim 1, wherein the signal generator comprises at least one of the following:
    a plurality of temperature sensors located at different parts of the band for detecting a temperature distribution across the band;
    a connection sensor configured to detect a disconnection between the band and the body;

a shape-memory alloy extending along the band, wherein the shape-memory alloy is configured to provide a resistance signal when the shape-memory alloy assumes a particular shape;

a heart rate detector configured to detect a heartbeat signal of a user when the band is placed in close proximity of a body part of the user;

a touch sensor for detecting a touch action on a surface of the band; or a signal transmitter configured to send the signal to a processor device.

9. A wearable device, comprising:
a body;
a band coupled with the body; and
a signal generator configured to generate a signal indicating a change of a relative position between the band and the body;
wherein the band and the body are coupled with each other by a connection pin;
wherein the signal generator comprises a sensor configured to detect the change of the relative position between the band and the body, wherein at least part of the sensor is integrated in the connection pin.

10. The wearable device of claim 9, wherein:
the relative position between the band and the body includes a relative angle between the band and the body.

11. The wearable device of claim 10, wherein the sensor comprises:
a magnetic device configured to establish a magnetic field in the connection pin; and
a wire made of electrically conductive material integrated in the connection pin, wherein the wire generates an electrical current by moving in the magnetic field when a relative angle between the band and the body changes.

12. The wearable device of claim 10, wherein the sensor comprises:
a capacitor including first and second panels, the first panel being integrated in the band or the body and the second panel being integrated in the connection pin, wherein the first and second panels of the capacitor are configured to cause a change of electrical charges held by the capacitor when a relative angle between the band and the body changes.

13. The wearable device of claim 10, wherein the sensor comprises:
a plurality of resistors integrated in the band or the body, the plurality of resistors having different resistance values; and
a contacting member on an outer surface of the connection pin, wherein the contacting member is configured to contact one of the plurality of resistors when the band and the body form a particular angle.

14. The wearable device of claim 9, wherein the signal generator comprises:
a connection sensor configured to detect a disconnection between the band and the body.

15. A band, comprising:
first and second bracelet links;
a connection pin linking the first and second bracelet links; and
a sensor configured to detect a relative position or a change of the relative position between the first and second bracelet links;
wherein the relative position between the first and second bracelet links includes a relative angle between the first and second bracelet links; wherein at least part of the sensor is integrated in at least one of the first bracelet link or the connection pin.

16. The band of claim 15, wherein:
each of the first and second bracelet links comprises a block portion and a distal portion, wherein the block portion includes a through hole, and the distal portion includes two receiving holes; and
the connection pin passes through the through hole of the block portion of the first bracelet link and is secured by the receiving holes of the distal portion of the second bracelet link at both ends of the connection pin,
wherein at least part of the sensor is integrated in at least one of the block portion of the first bracelet link or the connection pin.

* * * * *